United States Patent [19]

Perry, 3rd

[11] 3,940,905

[45] Mar. 2, 1976

[54] METHOD AND APPARATUS FOR MAKING A THERMAL COMPRESS

[76] Inventor: Thomas William Perry, 3rd, 474 Princeton Ave., Brick Town, N.J. 08723

[22] Filed: Aug. 2, 1974

[21] Appl. No.: 494,309

Related U.S. Application Data

[62] Division of Ser. No. 373,436, July 25, 1973, Pat. No. 3,865,117.

[52] U.S. Cl. .................... 53/14; 53/133; 53/182 R
[51] Int. Cl.² .................... B65B 9/02; B65B 61/18
[58] Field of Search ......... 53/14, 25, 180, 182, 133; 206/219, 220, 221, 222; 62/4; 229/56; 128/403; 156/199, 229, 324, 459, 156/468, 469; 126/263

[56] References Cited
UNITED STATES PATENTS

| | | | |
|---|---|---|---|
| 2,522,682 | 9/1950 | Lewis | 53/180 M |
| 3,085,681 | 4/1963 | Fazzari | 206/222 |
| 3,095,291 | 6/1963 | Robbins | 62/4 |
| 3,175,558 | 3/1965 | Caillouette | 128/403 |
| 3,255,872 | 6/1966 | Long | 206/219 |
| 3,391,047 | 7/1968 | Kopp | 206/219 X |
| 3,539,794 | 11/1970 | Rauhut | 206/221 X |
| 3,643,665 | 2/1972 | Caillouette | 206/219 X |
| 3,681,890 | 8/1972 | Pringle | 53/133 X |
| 3,756,389 | 9/1973 | Firth | 206/219 |
| 3,763,622 | 10/1973 | Stanley | 128/403 X |

Primary Examiner—Travis S. McGehee
Assistant Examiner—John Sipos

[57] ABSTRACT

A thermal compress has an outer container defining an inner space. An inner wall provided within the container divides the space into two separate compartments each bounded in part by the outer container in one embodiment of the invention. A control is physically associated with the wall to provide, on the application of manual forces to the container, a passage through the wall at a localized and predictable position. Different substances are respectively located in the above mentioned compartments and separated by the wall until the formation of the passage through the wall whereupon the substances contact each other and perform a thermal reaction to provide heat or cold. With respect to the outer container, two sheets are connected together to form the inner space with a wall being provided in the inner space to divide the same into two compartments with the aforesaid substances being respectively located in these compartments and adapted on contact to effect a thermal reaction. As one form of control, a tear strip is connected between the sheets and to the wall to enable tearing a passage into the wall to permit the substances to mix. Preferably the tear sheet is connected to the wall along a V-shaped seam adapted to form a passage through the wall at a localized and predictable position.

8 Claims, 8 Drawing Figures

METHOD AND APPARATUS FOR MAKING A THERMAL COMPRESS

OTHER APPLICATIONS

This application is a divisional application based on my earlier filed copending application Ser. No. 373,436 filed July 25, 1973 now U.S. Pat. No 3,865,117.

FIELD OF INVENTION

This invention relates to apparatus and methods for preparing thermal compresses adapted upon manipulation to provide a source of heat or a cooling compress and more particularly to apparatus and methods for manufacturing compresses as described in application Ser. No. 373,436.

BACKGROUND

It is known to provide thermal compresses in the form, for example, of a plastic envelope containing a chemical which absorbs heat on the addition of water thereto and in which the water is retained in a separate envelope which is susceptible of being ruptured so that the necessary thermal change or thermal reaction will take place when the water is permitted to come together with the aforementioned chemical. Such an article of manufacture is described, for example, in U.S. Pat. No. 2,907,173 which issued to A. Robbins on Oct. 6, 1959. In this patent is described a refrigerating package which includes an outer sealed envelope coated with a metallic foil and containing a dry freezing chemical mixture with a sealed envelope contained within the outer sealed envelope and containing a hydrous substance, the inner envelope being susceptible of being ruptured without breaking the outer envelope. This patent discloses, among other chemicals, the use of ammonium nitrate, sodium carbonate and the like which upon being exposed to water or to a hydrous chemical form a cooling mixture. The envelopes in which the chemicals are retained and in which the water or hydrous chemical are retained are fabricated, for example, of polyethylene, vinyl or acetate. The inner bag is sufficiently thin that when the compress is twisted or compressed, the inner envelope is torn permitting the material therein to escape and intermingle or mix with the other chemical contained in the outer envelope.

A further description of a thermal compress in the form of a refrigerating package is given in U.S. Pat. No. 2,925,719 which issued on Feb. 23, 1960 to A. Robbins et al. This patent describes a refrigerating package comprising a sealed outer envelope formed of flexible fluid-tight transparent sheet plastic material, a refrigerating chemical disposed within this outer envelope, a water soluble coloring dye disposed in the outer envelope and a sealed water containing inner envelope formed of a flexible fluid-tight transparent sheet plastic material disposed within the outer envelope. The inner envelope is of smaller dimensions and has a lower bursting strength than the outer envelope. The interior of the outer envelope is partially evacuated of air and the water within the inner envelope is normally isolated from the refrigerating chemical. The exterior surfaces of the walls of the inner envelope are directly engageable by the interior surfaces of the walls of the outer envelope whereby an inwardly directing force applied against the outer envelope imposes a direct mechanical force on the inner envelope to rupture the latter without breaking the outer envelope. Thereby there is effected the mixing of the water with the refrigerating chemical and with a coloring dye.

Among the problems of the packages provided by A. Robbins in the aforesaid patents is the problem that sometimes considerable force is required to burst the inner envelope in order to provide for a mixing of the thermally reactive chemicals. In addition it is sometimes found that a certain technique is required to burst the inner envelopes and that this technique is not always easily effected. In addition there are problems of premature liquid leakage and furthermore it is not possible to construct packages of predictable operation since it is not possible to predict where the inner envelopes will burst and the degree to which there will exist a passageway between the substance contained in the inner envelopes and the substance surrounding the same.

Some of the above problems are to a slight extent solved by Caillouette et al in U.S. Pat. No. 3,175,558 which issued on Mar. 30, 1965. Herein is described a therapeutic pack for the thermal treatment of a person which pack includes a container bag of flexible proof material, chemical substances within the container bag including a liquid component and a separate non-liquid component for producing a temperature changing reaction upon the mixture of these components within the bag, there being provided a fracturable section for containing the liquid component apart from the other component so that the components can be controllably mixed to give the desired thermal result. In this patent is furthermore described the coating of at least a portion of one of the chemical components with a soluble coating in order that the mixing of the substances be spread out over a greater period of time. In addition, there is described an absorbent pad corresponding in size to the container bag and a wrapper of flexible material for holding the pad and the container bag together whereby the pad can be held adjacent to the person being treated.

The difficulty with one embodiment of the invention disclosed by Caillouette et al is that the solid chemical substance is generally retained all in one portion of the resulting enclosure after the chemicals are permitted to mix, while at the same time, the package provided is of extended length and difficult to pack and ship as well as to manufacture with a high degree of consistency as regards the subsequent usage thereof. This embodiment employs opening tabs but employs them in a construction wherein the fluid forces which are exerted on the closure between the substances can be expected to lead to fluid leakage and consequently premature operation of the package. The other embodiment disclosed by Caillouette et al. is subject to the same deficiencies as have been noted hereinabove with respect to the Robbins Patents.

SUMMARY OF INVENTION

It is an object of the invention to provide improved apparatus and methods for manufacturing thermal compresses.

It is a further object of the invention to provide improved methods and apparatus for manufacturing an improved thermal compress having an improved style of operation.

Still another object of the invention is to provide improved methods and apparatus for manufacturing an improved thermal compress capable of retaining two substances in isolated relationship until the time arrives for the using of the compress at which time a passage can be provided between the substances at a localized and predictable location.

Another object of the invention is to provide improved methods and apparatus for manufacturing an improved thermal compress having a high degree of safety as regards the possibility of leakage of one substance into the other substance which is intended to react therewith.

Still another object of the invention is to provide improved methods and apparatus for manufacturing an improved thermal compress which requires a low degree of strength to provide for intermixing the substances which are to react thermally.

In application Ser. No. 373,436 there is described a thermal compress comprising an outer container defining an inner space, an inner wall within said container dividing said space into two separate compartments each bounded in part by said outer container, control means physically associated with said wall to provide, on the application of at least one manual force to the container, a passage through the wall at a localized and predictable position, and first and second chemicals respectively located in said compartments and separated by said wall until the formation of said passage, said first and second chemicals upon contacting one another, after the formation of said passage, performing a thermal function such as generating heat or providing for a cooling action.

In accordance with a preferred form described in application Ser. No. 373,436, the outer container includes two sheets connected together along a closed line through the intermediary of the aforesaid wall. Preferably the sheets and wall are peripherally sealed together.

According to a preferred embodiment of the invention in application Ser. No. 373,436, the aforementioned control means includes a tear strip connected to the aforesaid wall. Advantageously the sheets and wall are flexible and the control device is operatively associated therewith. Apart from being a tear strip as described above, the control means may be a generally rigid frangible member provided in the wall and adapted for being broken to provide the localized and predictably located passage.

The method of the invention for making the above-noted type of thermal compress comprises sandwiching a wall between two sheets and connecting the sheets to the wall along a closed line to form separate compartments which are charged with a respective thermally reactive substance. The method further comprises leaving an opening into each said compartment through the aforementioned line then charging the compartment with respective of said substances through the openings and then closing each said opening.

The walls and sheets are formed of a flexible plastic and are heat sealed along the aforesaid line. As provided in accordance with one embodiment of the invention, the wall may be provided with a rigid frangible part. According to another embodiment of the invention, the tear strip mentioned above is sealed to the above mentioned wall on one side of the latter and is, at its other extremity, sealed between the wall and one of said sheets.

The method of the invention includes bending the wall and the sheets as well as said tear strip transversely of the latter and, before the tear strip is sealed between the wall and the associated sheet, at least partly straightening the tear strip to decrease the effective length thereof relative to that of the wall and associated sheets.

As has been noted hereinabove the method of the invention may comprise sealing the tear strip to the one side of the wall along a V-shaped seam. The invention may comprise, as a particularly advantageous form thereof, loading foam plastic elements into at least one of the compartments to form an insulation layer.

The apparatus of the invention will comprise sources of three sheets of plastic, guides to guide the same into face-to-face relationship with one of the sheets sandwiched between the other two sheets to form a wall therebetween, sealing devices to seal the sheets together to form two pockets separated by the aforesaid wall and supplies to supply into respective of the pockets substances which when mixed result in a thermal change as noted hereinabove. In addition the apparatus will include sealing devices to seal the aforesaid pockets closed.

According to the invention, the apparatus provided in accordance therewith will include means to apply to the wall a device for controllably forming in the wall a passage through which the aforesaid substances can be mixed. The aforesaid means may include a source of a strip and a sealing means to seal the strip to the wall. Also there may be included means to bend the sheets and strip transversely of the latter and means to straighten the strip at least in part before the pockets are sealed closed.

The guides mentioned hereinabove may include at least one concave roller to provide for the admission of at least one of the substances into one of the pockets and to permit the above-mentioned straightening of the tear strip.

With the above indicated apparatus there may be formed a thermal compress comprising two sheets connected together to form an inner space, a wall in the inner space to divide the same into two compartments, chemicals in the compartments adapted on contact to effect a thermal reaction, and a tear strip connected between the sheets and to the side wall to enable a tearing of a passage into the wall to permit the substances to mix.

The construction may be such that the compartments are preferably and respectively bounded by the aforesaid sheets. However, it is also possible that the tear strip may be used in a construction where the compartments are arranged so that one of these compartments is spaced from the associated sheets.

The above objects and features of the invention as well as advantages thereof will be better understood from the following detailed description of some preferred embodiments as illustrated in the accompanying drawing.

DETAILED DESCRIPTION

The invention is generally concerned with a method and apparatus for manufacturing a thermal compress which can be operated by means of an activator strip or the like or by the use of a precisely located rigid and frangible member. The thermal compress enables the use of a foam plastic of greater thickness or of desired thickness for the separator walls or inner envelopes to avoid leakage problems while still enabling the facile actuation of the chemicals.

The invention relates moreover to methods and apparatus for forming a plurality or multitude of compartmented bags which can be activated as has been described generally above while being capable of being automatically fabricated. The techniques of the invention can be used with therapeutic hot packs or cold packs in turn involving exothermic or endothermic reactions.

By the use of the expression "thermal compress" is intended to be meant packages capable upon manipulation of mixing two previously isolated chemicals or substances to perform a thermal reaction which is either exothermic or endothermic, as noted above, whereby in one type of package depending upon the chemicals involved there may be generated heat while in another type of package due to the chemicals involved there may be generated a cooling effect.

Figure 2:
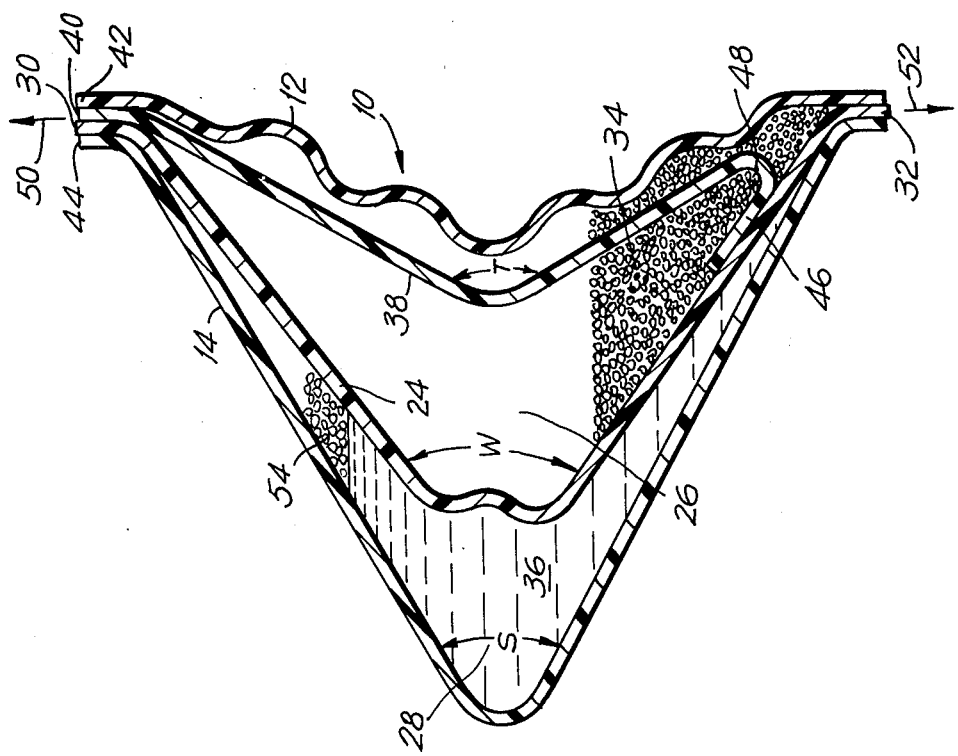
FIG. 2 is a sectional view taken along section II—II of FIG. 1.
Figure 1:
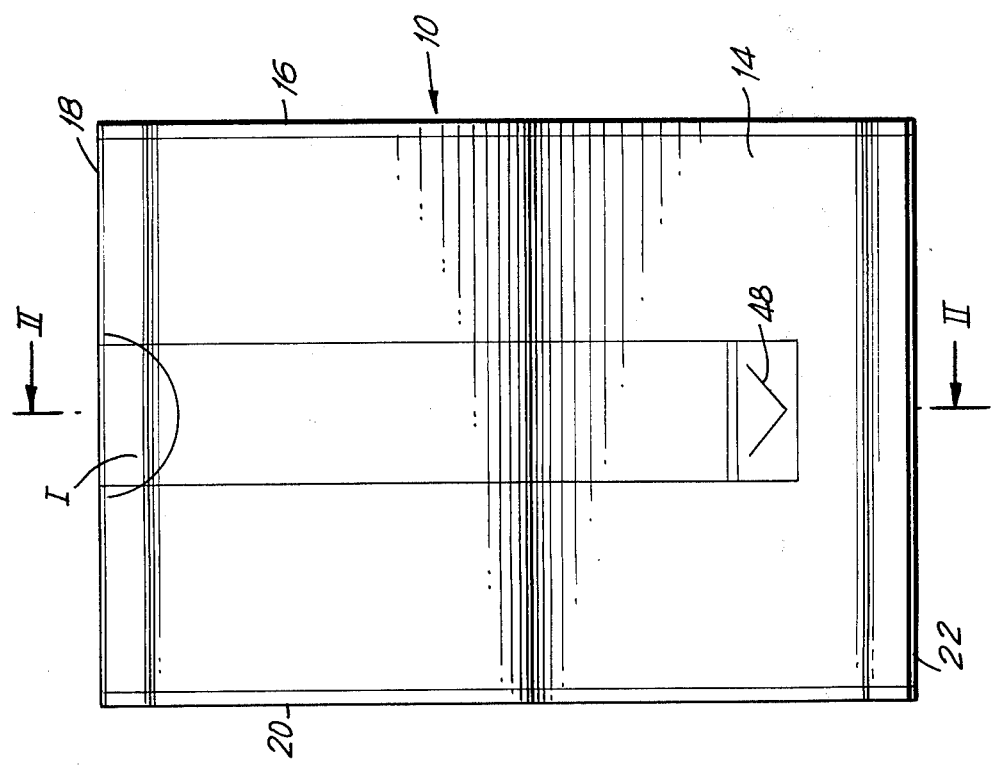
FIG. 1 is a front view of a thermal compress prepared in accordance with one embodiment of the invention.

In the FIGS. 1 and 2 is illustrated a thermal compress 10 which includes two outer walls or sheets 12 and 14 sealed together along edges 16, 18, 20 and 22.

Sandwiched between the sheets 12 and 14 is a third sheet 24 which constitutes a separator wall which divides the inner space formed between the sheets 12 and 14 into two compartments 26 and 28. It will be particularly noted in FIG. 2 that the wall 24 is peripherally sealed to the sheets 12 and 14 as, for example, indicated at 30 and 32.

In the compartment 26 is contained a chemical 34 such as has been noted above and inclusive by way of example of the following: $Na_2CO_3 \cdot H_2O$; $NH_4Cl$; $Na_2SO_4$; $KI$; $CaCl_2$; and $NH_4NO$.

In the compartment 28 is located a hydrous chemical or water 36 capable, on intermixing with the chemical 34, of effecting an exothermic or endothermic reaction as has been mentioned hereinabove.

To provide for a passage in a localized and predictable position so that the fluid in compartment 28 can pass into the compartment 34 and vice-versa, there is included in accordance with the invention a tear strip 38. This tear strip is connected at its extremity 40 between the edges 42 and 44 of sheets 12 and 14 respectively. At its other extremity, it is connected such as by heat sealing to the wall 24. This latter extremity is indicated at 46, there being a reversed bend 48 provided in the tear strip 38 as results from the manufacturing technique to be described hereinafter.

In FIG. 1, it will be noted that the connection between the extremity 46 of tear strip 38 to the wall 24 is provided along a V-shaped seam 48, the purpose of this seam being to provide a localized and highly predictable position for the passage to be formed upon the manipulation of the thermal compress of the invention as next described hereinbelow.

Examination of FIG. 2 will show that the effective lengths of sheets 12 and 14 as well as wall 24 is greater than the effective length of the tear strip 38. Sheet 14 and wall 24 have a greater effective length than tear strip 38 between the respective ends thereof due to the fact that the angle T formed by the tear strip 38 is smaller than the angle W formed by the wall 24 and the angle S formed by the sheet 14. Tear strip 38 has a shorter effective length than the sheet 12 because the latter is wrinkled or, in other words, follows a serpentine path due to the bending or folding of the thermal compress. As a result, when the extremities of the thermal compress are pulled in the direction indicated by the arrows 50 and 52, by forces exerted at indicator I and at a position opposite the same, the tear strip 38 will be the first element of the aforediscussed elements to reach its fully extended length and thereafter the forces will cause the extremity 46 to pull against the wall 24 whereupon a passage will be initiated along the seam 48 which as been discussed hereinabove. This passage will be highly localized and highly predictable since it will occur specifically at the seam 48 and will occur upon the facile administration of forces of a relatively low magnitude.

It is to be noted that the tear strip 38 may be fabricated of a plastic which is preferably of a larger gauge than the gauge of the sheets 12 and 14 and the sheet or wall 24. All of these elements can be fabricated of a plastic such as, for example, polyethylene, vinyl or any other suitable plastic capable of retaining water or a hydrous chemical and inert to the chemicals concerned. As will be seen hereinafter, the outer sheets as well as the separator wall may be connected along a closed line, the sheets and wall being preferably peripherally sealed together.

Indicated at 54 are a plurality of foam plastic elements such as small plastic balls or spheres which, when the device is operated to mix the thermally reacting chemicals, will float on the liquid and form an insulating layer. This feature can advantageously be employed to prolong the cold effect or to prevent excessive heat from reaching the skin in case of the provision of a therapeutic hot pack.

Figure 3:
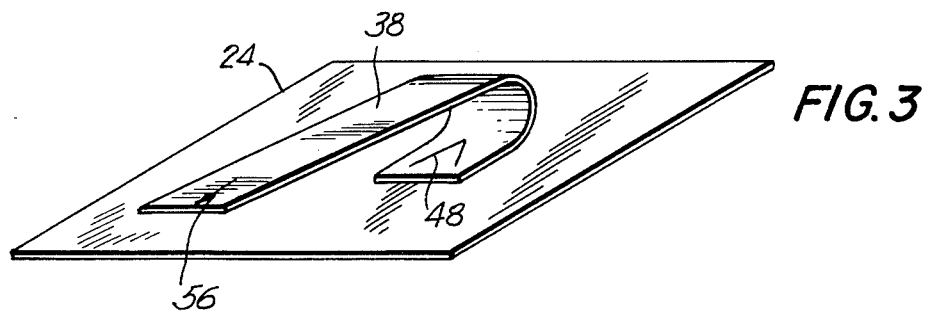
FIG. 3 is a diagrammatic illustration of the operation of the tear strip of the invention.

FIG. 3 diagrammatically illustrates the effect of the tear strip 38 with respect to the wall 24. When the force indicated by arrow 56 is exerted on the extremity of the tear strip 38 which is not connected to the wall 24, the aforesaid passage will result along the V-shaped seam 48. It is to be noted that by use of the term "V-shaped", it is not intended to limit the invention to the precise shape of a V since it will be clear that W-shaped seams and certain U-shaped seams and the like will also be capable of providing a localized and positionally predictable opening in the wall 24 in accordance with the invention although the V-shape will be best.

Figure 4:
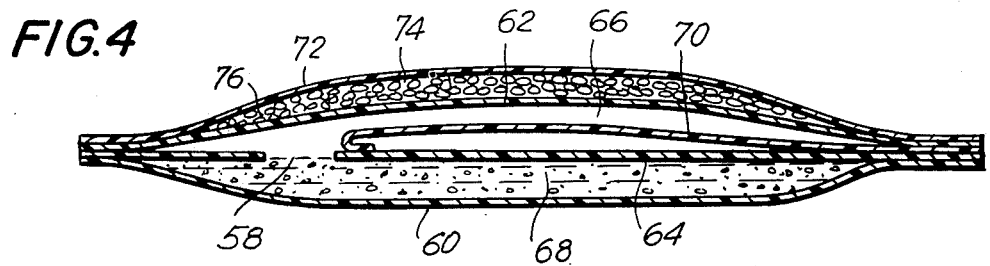
FIG. 4 illustrates a further thermal compress straightened out to tear a passage into the intervening wall.

FIG. 4 illustrates a further compress somewhat similar to that illustrated in FIGS. 1 and 2, the view in FIG. 4 illustrating the associated thermal compress after it has been straightened out to form the passage 58 and to provide for a mixing of the thermally active chemical reactants.

In FIG. 4 is illustrated a thermal compress including sheets 60 and 62 defining an inner space which is divided by a wall 64 into compartments 66 and 68 wherein the chemical substances mentioned hereinabove are respectively located. The construction also includes a tear strip 70 of the aforementioned type which is connected in the same manner as described above to provide eventually the passage 58.

In the construction of FIG. 4, there is additionally attached a plastic sheet 72 to provide a further compartment 74 wherein are located a multitude of foam plastic elements or spheres 76 which provide an insulating effect as has been described above.

Figure 5:
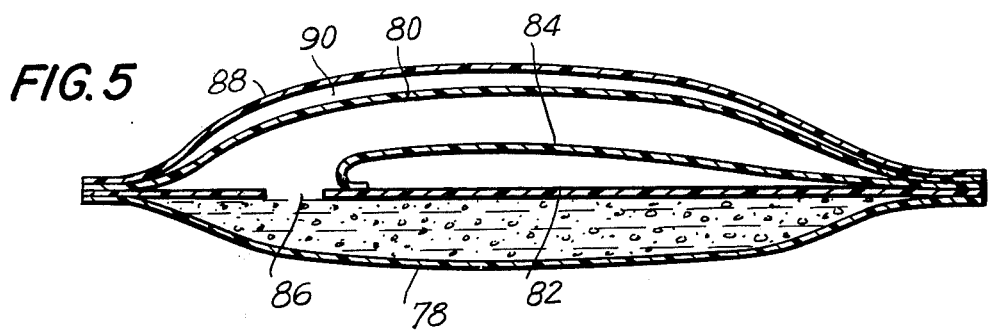
FIG. 5 is a view similar to FIG. 4 illustrating a further compress.

FIG. 5 is a view similar to FIG. 4, showing a further compress, including walls 78 and 80 and further including the intervening wall 82 with which is associated the tear strip 84 for forming the passage 86 in the above-noted manner.

The construction of FIG. 5 inlcudes a further sheet 88 forming an additional compartment 90 which is filled with air in order to space the wall 88 from the sheet 80 whereby to provide for ameliorating the heating or cooling effect as applied to the skin of the person using the device or being treated with the same.

Figure 6:
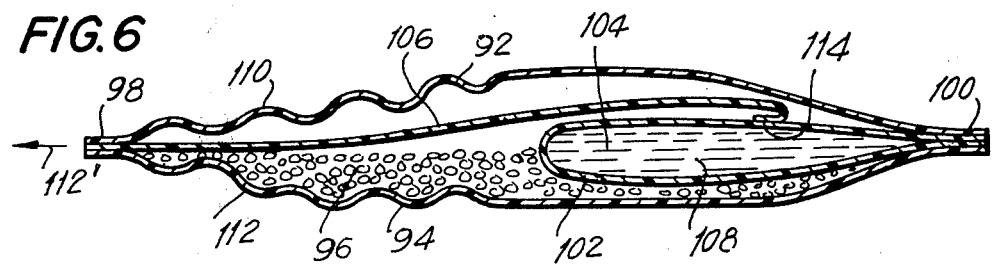
FIG. 6 illustrates a further embodiment of the wherein the tear strip is employed with a compartment contained in entirety within an outer container.

The construction of FIG. 6 is also a thermal compress. It comprises the outer sheets 92 and 94 forming an inner space 96 and peripherally connected at edges 98 and 100. In this embodiment of the invention an inner wall 102 provides an inner compartment 104 entirely separated from the sheets 92 and 94 as distinguished from the forms mentioned hereinabove. In each of the forms mentioned hereinabove, the inner compartments are bounded by the associated outer sheets whereas in the forms of FIG. 6, as has been mentioned above, the inner compartment is isolated from the sheets 92 and 94. The construction of FIG. 6 has in common with the aforegoing forms, the provision of the tear strip 106 which operates in the manner mentioned hereinabove to provide a passage through which can flow the fluid or hydrous chemical 108 contained within the compartment 104.

In the construction of FIG. 6, the left extremities of the sheets 92 and 94, such as indicated at 110 and 112 are wrinkled or folded or otherwise follow a serpentine contour so that a straightening of the same will apply to the tear strip 106 a force as indicated by arrow 112 to provide that the extremity 114 of the tear strip 106 generate in the compartment 104 a passage which is highly localized and predictably located.

Figure 7:
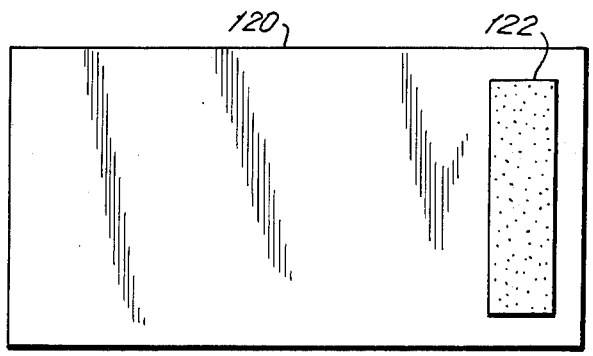
FIG. 7 is a plan view of an intervening wall employed in a further compress.

A further compress is illustrated in FIG. 7 wherein the plan view of the wall 120, which is the separator wall between the two compartments, is sufficient to understand the operation of the resulting thermal compress. Herein, the wall 120 includes a section 122 which is of a preferably rigid and frangible substance such as a plastic foam or the like.

It will be understood that since the wall 120 is of a flexible plastic, the provision of the frangible member 122 enables the breaking of the latter by a distortion of the wall 120 and the associated outer walls of the package whereby a highly localized and predictably located passage is provided in the wall 120 to enable an intermixing of the aforesaid chemicals.

Figure 8:
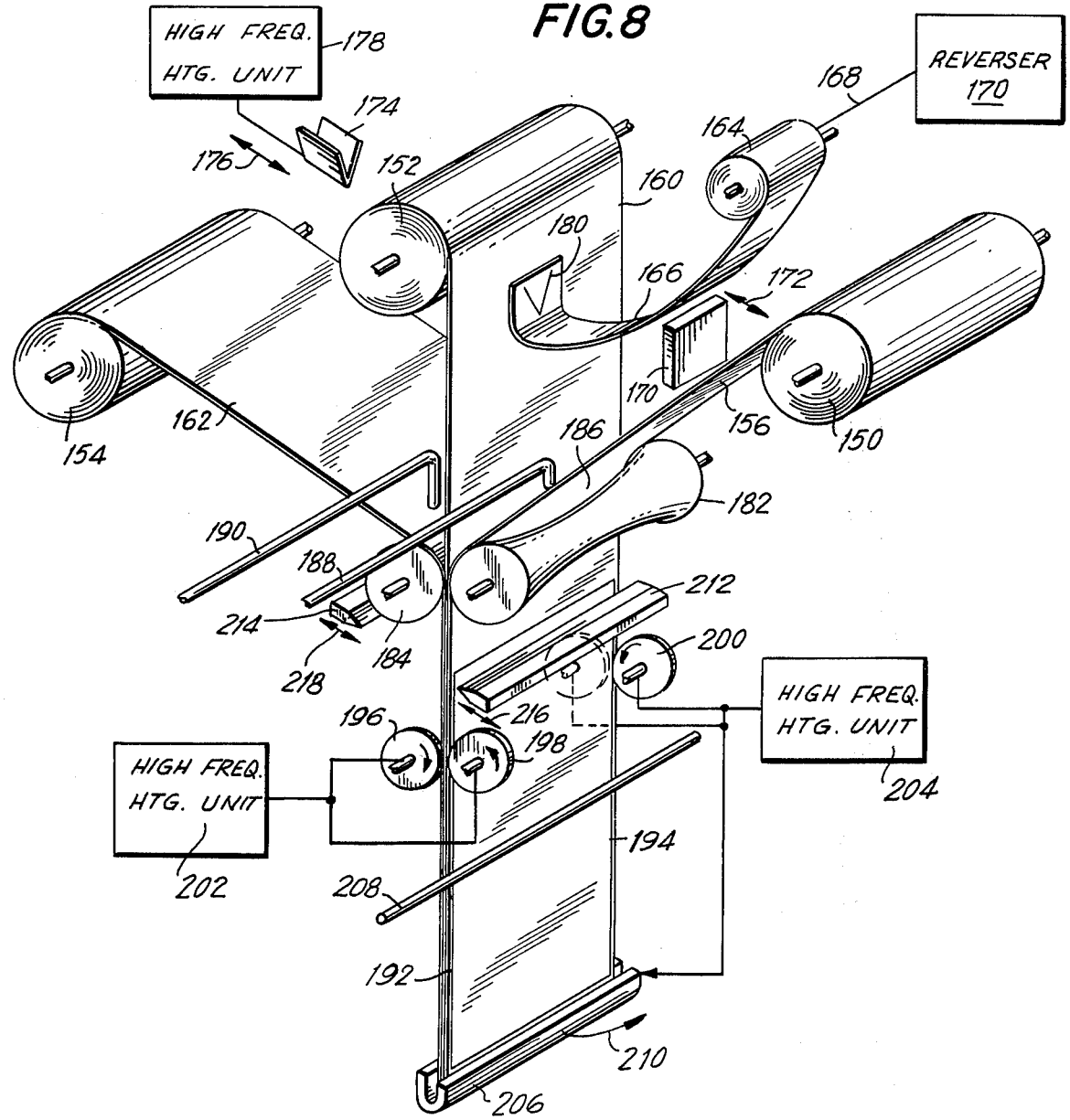
FIG. 8 diagrammatically illustrates the method and apparatus of the invention.

The method and apparatus of the invention are best understood by reference to FIG. 8 wherein appear sources 150, 152 and 154 of plastic sheets 156, 160 and 162 respectively, said sheets forming the outer sheets of the resulting thermal compress with the central sheet 160 forming the separator wall utilized therein.

Also provided is a source 164 of the tear strip 166, said source being connected by a mechanical means 168 with a reverser drive 170 for a purpose which will be described hereinafter.

For attaching the strip 166 to the central sheet 160 which forms the separator wall, there is provided a back up block 170 capable of being reciprocally moved as indicated by arrow 172 and operating in conjunction with the sealing member 174 also capable of being operated in reciprocal directions as indicated by the arrow 176. A source of heat can be provided, for example, in the form of a high-frequency heating unit 178 of known construction. Alternatively, different sources and forms of heat can be employed. The function of the sealing member 174 is, as will be consistent with the aforegoing description, to provide a V-shaped seal as indicated at 180 or a seal which is equivalent thereof so that a passage can be torn in the wall 160 in the manner which as been described hereinabove.

The apparatus illustrated in FIG. 8 includes a guide consisting in part of rollers 182 and 184, these rollers being preferably concave in order to provide sections such as indicated at 186 for the introduction of the different chemical substances by means of nozzles 188 and 190 or the like. In the event that foam plastic elements or spheres, as have been described above, are to be introduced, an additional source or nozzle (not shown) may be employed.

To seal the sheets 156, 160 and 162 laterally together at their extremities which are indicated at 192 and 194, there are provided rotary sealing elements 196, 198 and 200 as well as a fourth sealing element cooperating with the element 200 and concealed from view by the aforementioned sheets. The elements 196, 198 and 200 are rotary elements and are supplied with energy by high-frequency units 202 and 204 which may be of any known construction. The rotary elements serve also to pull the sheets downwardly.

The lower extremity of the aforesaid sheets are received in a channel 206 whereat they are sealed together by energy supplied by high-frequency heating unit 204. It is to be understood that the arrangement indicated by sealing members 196, 198 and 200 as well as by element 206 is very diagrammatically indicated and that the detailed construction of these components of this apparatus will be obvious to those of ordinary skill in the art involved.

A bar extending transversely of the aforesaid sheets is indicated at 208. Movement of the member 206 in the direction indicated by the arrow 210 will cause a bending of the three aforesaid sheets 156, 160 and 162 as well as of the strip 166 connected to the center sheet or wall 160. The member 206 is then returned to the illustrated position which will allow a certain amount of slack in the sheets 156, 160 and 162 as well as in the strip 166. The sheets 156, 160 and 162 will, however, not be drawn in reverse direction due to peripheral engagement by the rollers 182 and 184 which turn unidirectionally only. At this time, however, the direction of rotation of the source or roller 164 is reversed by reverser drive 170 whereby the strip 166 is drawn taut or is effectively shortened in length to have a shorter effective length than the folded or bent sheets 156, 160 and 162. This will have the effect of creating a unit such as has been discussed relative to FIG. 2 above.

Finally, there are diagrammatically illustrated cutter blades 212 and 214 capable of moving in reciprocal directions as illustrated by arrows 216 and 218 in order to sever and seal the aforesaid sheets as well as the tear strip 166 connected to the separator wall 160. The strip 166, however, will have a shortened effective length due to operation of reverser 170. Thereby in accordance with the invention, there may be formed the compresses illustrated in FIGS. 1 and 2 above and with minor modifications and changes, the compress illustrated in FIGS. 4 and 5.

From what has been described above, it will now be obvious that the invention provides a method of making a thermal compress comprising sandwiching a wall between two sheets and connecting the sheets to the wall along a closed line to form separate compartments which are respectively charged with thermally reactive substances. An opening is left in each of the compartments so that the compartments can be charged with respective of the chemical substances mentioned above whereafter the openings can then be sealed off. This sealing operation can be effected through the aforesaid cutters 212 and 214 which may be, for example, coupled to the high-frequency heating units 202 or 204.

The method of the invention comprises forming the aforesaid wall and sheets of flexible plastic such as polyethylene, vinyl or the like and heat sealing the same along the aforesaid closed line.

Alternatively, the method may comprise forming the separator wall with a rigid frangible part.

According to the preferred embodiment of the invention, a tear strip is sealed to the separator wall on one side of the latter and the opposite extremities of the tear strip is sealed between the separator wall and one of the associated sheets.

The method of the invention furthermore comprises bending the wall and sheet, as well as the tear strip, transversely of the latter and, before the tear strip is sealed between the said wall and said one sheet, at least partly straightening the tear strip to decrease the effective length thereof relative to that of the wall and sheets.

Preferably, the tear strip is sealed to one side of the wall along a V-shaped seam or the like.

As a feature of the invention the method thereof may comprise loading foam plastic elements or pellets into at least one of the compartments to form an insulation layer. Further sheets may be attached to the aforegoing package in order to provide for insulation spaces including air or plastic pellets or alternatively, being evacuated and supplied with an inert gas or the like.

The apparatus of the invention as has been seen comprises sources of three sheets of plastic, guides to guide the same into face-to-face relationship with one of the sheets sandwiched between the other two sheets, sealing devices to seal the sheets together to form two pockets separated by one of the sheets which forms the separator wall, supplies to supply into respective of the pockets substances which when mixed result in a thermal change and a sealing device to seal the pockets closed.

There will now be obvious to those skilled in the art many modifications and variations of the methods and apparatus described hereinabove. These modifications and variations will not depart from the scope of the invention if defined by the following claims.

What is claimed is:

1. A method of making a thermal compress comprising sandwiching a wall between two sheets and connecting the sheets to the wall along a closed line to form separate compartments, sealing a tear strip between said wall and one of said sheets, bending said wall and sheets as well as said tear strip transversely of the latter and, before the tear strip is sealed between said wall and said one sheet, at least partly straightening the tear strip to decrease the effective length thereof relative to that of said wall and sheets.

2. A method as claimed in claim 1 comprising sealing the tear strip to said wall along a V-shaped seam.

3. A method as claimed in claim 2 comprising loading foam plastic elements into at least one of said compartments to form an insulation layer.

4. Apparatus for manufacturing a thermal compress comprising sources of three sheets of plastic, guide means to guide the same into face-to-face relationship with one of the sheets sandwiched between the other two sheets, sealing means to seal the sheets together to form two pockets separated by said one sheet which constitutes a wall between the pockets, supply means to supply into respective of said pockets substances which when mixed result in a thermal change, sealing means to seal the pockets closed, a source of a strip, sealing means to seal said strip to said wall, means to bend the sheets and strip transversely of the latter, and means to straighten the strip at least in part before the pockets are sealed closed.

5. Apparatus as claimed in claim 4 comprising further means to apply to the wall a device for controllably forming in the wall a passage through which said substances can be mixed.

6. Apparatus as claimed in claim 5 wherein the sealing means to seal the pockets closed is positioned to seal said strip in one of said pockets when the latter are sealed shut.

7. Apparatus as claimed in claim 6 wherein the sealing means to seal the strip to the wall includes a member shaped to form a V-shaped seam.

8. Apparatus as claimed in claim 6 wherein said guiding means includes at least one concave roller to provide for the admission of one of said substances into one of said pockets and to permit straightening of said strip.

* * * * *